(12) United States Patent
Tachibana et al.

(10) Patent No.: US 6,219,401 B1
(45) Date of Patent: Apr. 17, 2001

(54) PANORAMIC RADIOGRAPHIC APPARATUS AND DIGITAL SENSOR CASSETTE USED FOR SAME APPARATUS

(75) Inventors: Akifumi Tachibana; Takeshi Hayashi; Masakazu Suzuki; Junichi Furukawa; Yutaka Ito; Masaya Tatsumi; Hideki Yoshikawa, all of Kyoto (JP)

(73) Assignee: Kabushiki Kaisha Morita Seisakusho, Kyoto (JP)

( * ) Notice: Subject to any disclaimer, the term of this patent is extended or adjusted under 35 U.S.C. 154(b) by 0 days.

(21) Appl. No.: 09/547,377

(22) Filed: Apr. 11, 2000

Related U.S. Application Data

(62) Division of application No. 09/154,674, filed on Sep. 18, 1998.

(30) Foreign Application Priority Data

Sep. 30, 1997 (JP) .................................................. 9-284451
Sep. 30, 1997 (JP) .................................................. 9-284452

(51) Int. Cl.[7] .................................................. A61B 6/14
(52) U.S. Cl. .............................................. 378/39; 378/98.8
(58) Field of Search .................................. 378/38, 39, 40, 378/98.8, 189; 250/370.09, 370.11

(56) References Cited

U.S. PATENT DOCUMENTS 5,018,177 * 5/1991 McDavid et al. ...................... 378/62
5,579,361 11/1996 Augais et al. .
5,784,429 * 7/1998 Arai ........................................ 378/38
5,844,961 * 12/1998 McEvoy et al. ..................... 378/98.8

FOREIGN PATENT DOCUMENTS 9-135829  5/1997  (JP) .

* cited by examiner

Primary Examiner—David P. Porta
(74) Attorney, Agent, or Firm—Koda & Androlia

(57) ABSTRACT

The panoramic radiographic apparatus of the present invention has a cassette holder capable of accommodating both a conventional film cassette and a digital sensor cassette loaded with an electric X-ray image detector, one at a time, in a rotary arm, wherein when a film cassette is mounted, the cassette holder is mechanically moved in accordance with the rotation of the rotary arm so as to carry out panoramic radiographing, and when a digital sensor cassette is mounted, without moving the cassette holder, the electric X-ray image detector is driven by supplying control signals corresponding to the rotation of the rotary arm to the digital sensor cassette to obtain image signals required for generating a panoramic X-ray image. Therefore, both the film cassette and the digital sensor cassette can easily be mounted, one at a time, whereby required panoramic X-ray images can be obtained by fully using the features of each type of cassette.

10 Claims, 11 Drawing Sheets

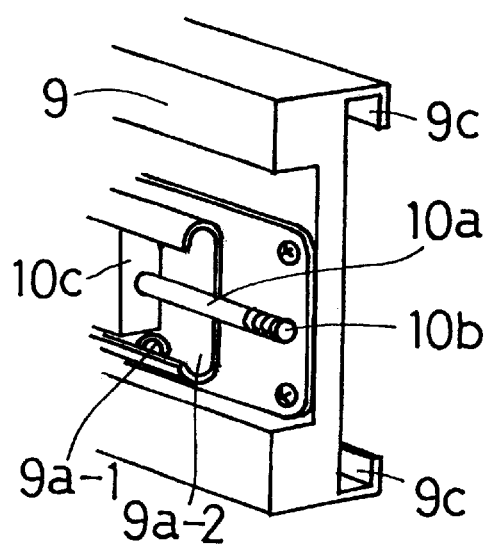 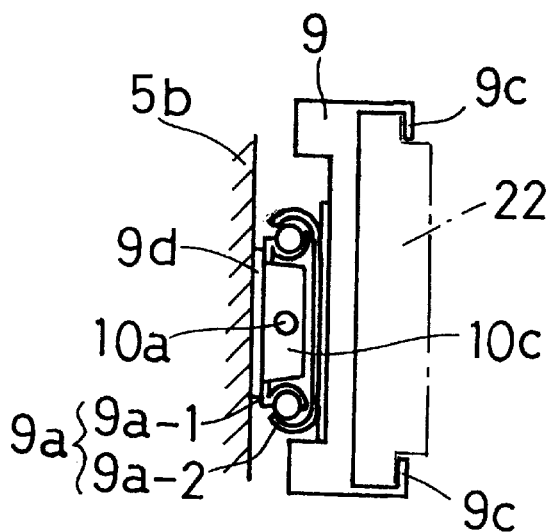
FIG. 6A  FIG. 6B
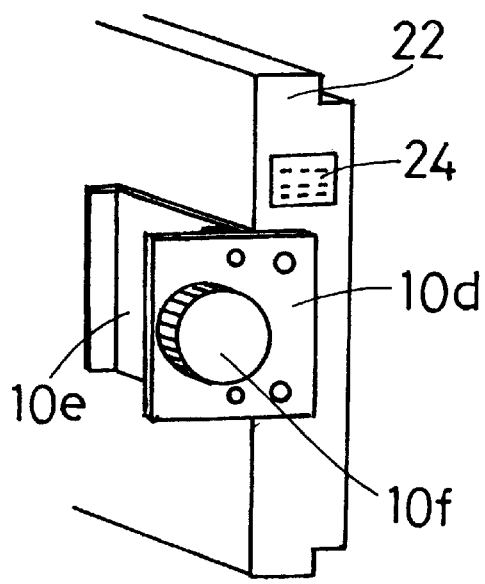 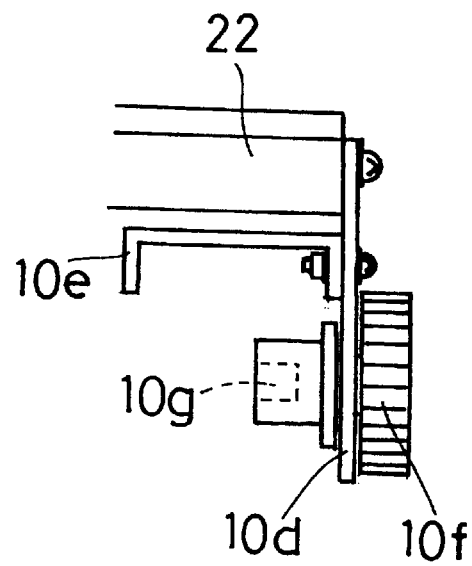
FIG. 7A  FIG. 7B

PANORAMIC RADIOGRAPHIC APPARATUS AND DIGITAL SENSOR CASSETTE USED FOR SAME APPARATUS

This is a divisional application of application Ser. No. 09/154.674, filed Sep. 18, 1998.

BACKGROUND OF THE INVENTION

1. Field of the Invention

The present invention relates to a panoramic radiographic apparatus for entire jaw photographing and the like in dental examination and treatment for example, and to a digital sensor cassette used for the same apparatus.

2. Description of the Prior Art

A panoramic radiographic apparatus used in dental, otorhinolaryngologic and other clinics has a support for rotatably supporting a rotary arm provided with an X-ray generator at one end thereof and an X-ray detector at the other end thereof, and a film cassette loaded with an X-ray film is mounted in the X-ray detector and moved at a predetermined speed in accordance with the rotation of the rotary arm so as to carry out panoramic radiographing. In addition, it is also known that instead of the film cassette, a digital sensor cassette loaded with an electric X-ray image detector is mounted in the X-ray detector, and the electric X-ray image detector is driven under the control of control signals corresponding to the rotation of the rotary arm so as to obtain image signals required for generating a panoramic X-ray image (for example, in Japanese Laid-open Patent Application No. Hei 9-135829 and U.S. Pat. No. 5579361).

The apparatus disclosed in Japanese Laid-open Patent Application No. Hei 9-135829 is provided with both a film cassette and a digital sensor cassette so that either cassette can be selectively used depending on the object of operation, whereby the trouble of replacement is eliminated, and examination and treatment can be made speedily. However, the structure of the X-ray detector becomes complicated, an X-ray detector for generally-used film cassettes cannot be used, that is, a special X-ray detector is necessary. Furthermore, the digital sensor cassette is built in the apparatus and does not have a structure to be inserted into and withdrawn from a cassette holder. Moreover, the configuration of the digital sensor cassette as a single cassette has not been disclosed specifically.

In the apparatus disclosed in the USP, a digital sensor cassette is mounted in a cassette holder, and this cassette holder is moved. In addition, a structure for detecting the speed of the movement is necessary, making the structure of the X-ray detector complicated. Furthermore, there is no concrete disclosure indicating any structure for replacing the film cassette with the digital sensor cassette, whereby the replacement is made with difficulty.

Furthermore, a panoramic radiographic apparatus using a digital sensor is superior to a panoramic radiographic apparatus using a film in that because no development is necessary, a panoramic X-ray image can be obtained immediately and can be widely used for examination and treatment through the use of computers. However, almost all the panoramic radiographic apparatuses used in clinics are types used with film cassettes, and cannot be used with digital sensor cassettes. For these reasons, if the panoramic radiographic apparatuses used with film cassettes can be used with digital sensor cassettes by slight modifications, a great advantage can be expected.

SUMMARY OF THE INVENTION

In accordance with the above, an object of the present invention is to provide a panoramic radiographic apparatus wherein both a film cassette and a digital sensor cassette can easily be mounted in and removed from the X-ray detector of the apparatus, one at a time, without making the structure of the X-ray detector complicated. Another object of the present invention is to provide a digital sensor cassette compatible with the film cassette.

In order to attain the above-mentioned objects, the panoramic radiographic apparatus of the present invention is an apparatus having a support for rotatably supporting a rotary arm provided with an X-ray generator at one end thereof and an X-ray detector at the other end thereof, comprising a cassette holder capable of accommodating both a film cassette loaded with an X-ray film and a digital sensor cassette loaded with an electric X-ray image detector, one at a time, at the X-ray detector, and a control means for performing electric control so that when a film cassette is mounted in the cassette holder, the cassette holder accommodating the film cassette is mechanically moved in accordance with the rotation of the rotary arm at a predetermined speed in a direction nearly perpendicular to X-ray beams applied from the X-ray generator to the X-ray detector so as to carry out panoramic radiographing using a film, and so that when a digital sensor cassette is mounted in the cassette holder, with the cassette holder accommodating the digital sensor cassette being in a secured condition with respect to the X-ray detector, the electric X-ray image detector is driven by supplying control signals corresponding to the rotation of the rotary arm from the main body of the panoramic radiographic apparatus to the digital-sensor cassette to obtain image signals required for generating a panoramic X-ray image.

The digital-sensor cassette for the panoramic radiographic apparatus of the present invention comprises at least an electric X-ray image detector disposed in face-to-face relationship with the X-ray generator via an X-ray shield plate having a secondary slit and provided at the X-ray detector, driven by control signals supplied from the main body of the panoramic radiographic apparatus in correspondence with the rotation of the rotary arm, and used to convert X-rays to electric signals to deliver image signals required for generating a panoramic X-ray image; an A/D converter for converting analog signals delivered from the electric X-ray image detector into digital signals; an input/output portion for communicating with an external circuit; and a control portion for electrically controlling the operations of the above-mentioned various portions. The outer housing of the digital sensor cassette is nearly identical with a conventional film cassette loaded with an X-ray film in shape, and the digital sensor cassette can be mounted in the cassette holder for the film cassette, provided at the X-ray detector of the panoramic radiographic apparatus.

With these configurations, both the film cassette and the digital sensor cassette can easily be mounted in the cassette holder of the panoramic radiographic apparatus, one at a time, whereby required panoramic X-ray images can be obtained by fully using the features of each type of cassette.

The concrete configurations of the panoramic radiographic apparatus and the digital sensor cassette of the present invention will be clarified by the following descriptions regarding embodiments.

BRIEF DESCRIPTION OF THE DRAWINGS

FIG. 6A is a perspective view showing the main portion of the film cassette;

FIG. 6B is a side view showing the main portion of the film cassette;

FIG. 7A is a perspective view showing the main portion of the digital sensor cassette;

FIG. 7B is a plan view showing the main portion of the digital sensor cassette;

DETAILED DESCRIPTION OF THE PREFERRED EMBODIMENTS

Next, embodiments of the present invention will be described below.

Figure 1:
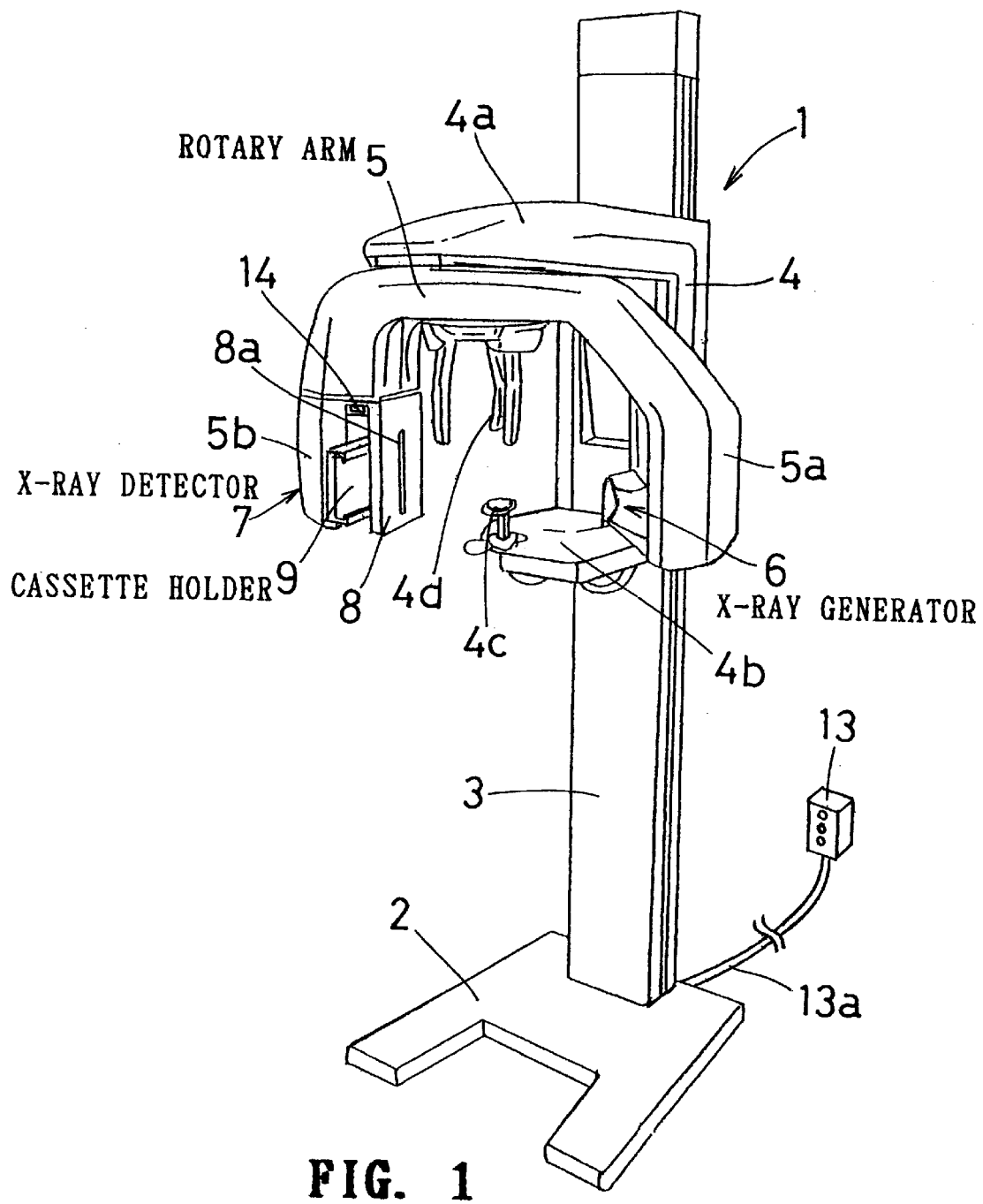
FIG. 1 is a perspective overall view showing a panoramic radiographic apparatus in accordance with an embodiment of the present invention.

Referring to FIG. 1, the numeral 1 designates the main body of a panoramic radiographic apparatus. A column 3 stands on a base 2, and a support 4 is mounted on the column 3 so as to be movable vertically. A rotary arm 5 is rotatably mounted on the support 4. A support arm 4a and a patient frame 4b, both extending in the horizontal direction, are provided at the upper and lower ends of the support 4, respectively. The patient frame 4b is provided with a chin rest 4c. The support arm 4a accommodates an XY table capable of being moved freely in the X and Y directions by stepping motors. The rotary arm 5 is suspended via this XY table so as to be movable as desired in a horizontal plane. The numeral 4d designates a patient's head holder disposed passing through the rotary arm 5 on the lower surface of the support arm 4a. The head holder 4d is equipped with a position adjustment mechanism.

The rotary arm 5 is provided with a rotary mechanism for rotating the rotary arm 5 around the support arm 4a by using a stepping motor. The rotary arm 5 is configured so as to rotate around its vertical axis while its rotation center is moved by the XY table. The rotary arm 5 has hanging portions at both ends thereof. An X-ray generator 6; is provided at one end 5a of the rotary arm 5, and an X-ray detector 7 is provided at the other end 5b in face-to-face relationship with each other. The X-ray generator 6 is equipped with an X-ray tube, an X-ray shield plate having a vertical primary slit, an adjustment mechanism for changing the shape of the primary slit and the like.

Figure 2:
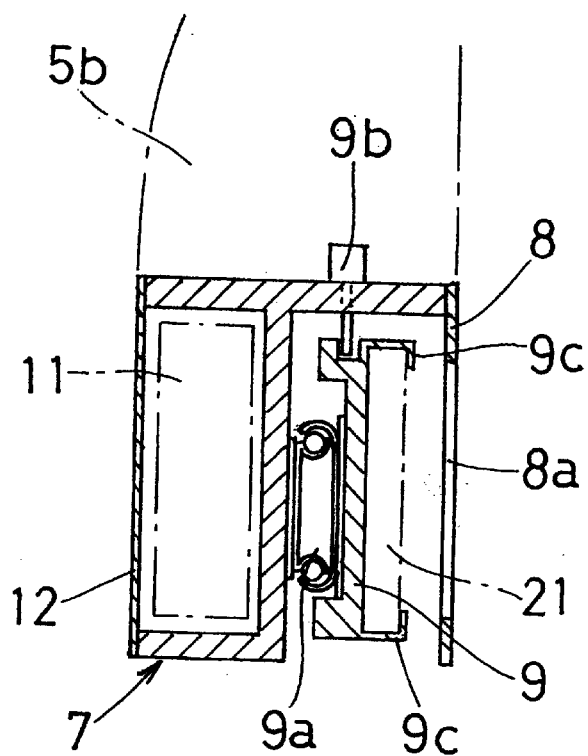
FIG. 2 is a sectional view showing the X-ray detector of the apparatus.

A shield plate 8 having a vertical secondary slit 8a corresponding to the primary slit and an adjustment mechanism for the secondary slit 8a is provided at the X-ray detector 7 in face-to-face relationship with the X-ray generator 6. Behind the shield plate 8, a cassette holder 9 is disposed. As shown in FIG. 2, the cassette holder 9 is supported by a slide bearing 9a so as to be movable in the horizontal direction perpendicular to the surface of the drawing in FIG. 2. The cassette holder 9 is provided with a drive motor 9b.

A control portion 11 comprising a PC board having a variety of circuits, and an operation panel 12 for covering the outside the control portion 11 are provided behind the slide bearing 9a of the X-ray detector 7. Various switches and a liquid crystal display portion (not shown) are mounted on the operation panel 12. In addition, a remote-control box 13 is provided, which is connected to the main body 1 of the apparatus via an operation cord 13a. The remote-control box 13 is provided with a main switch for power on/off operation and an X-ray irradiation switch, for example.

Figure 3:
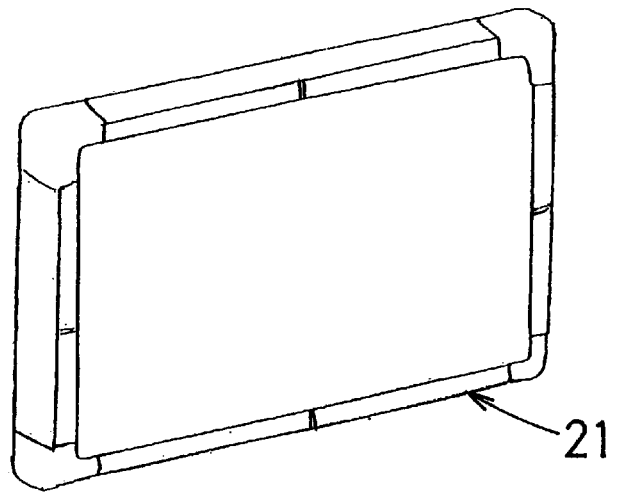
FIG. 3 is a perspective view showing an example of a film cassette for the apparatus.

When entire-jaw panoramic radiographing is carried out by using a film, the head of a patient is secured to a predetermined position on the patient frame 4b, and a film cassette 21 loaded with an X-ray film is mounted in the cassette holder 9 as shown in chain lines in FIG. 2. X-rays are then applied from the X-ray generator 6 to the X-ray detector 7. While the rotary arm 5 is rotated, the center of the rotation is moved along a predetermined track. In synchronization with this movement, the cassette holder 9 accommodating the film cassette 21 is moved together with the cassette 21 in the horizontal direction at a predetermined speed. This movement is carried out by the drive motor 9b. The direction of the movement with respect to the X-ray detector 7 is almost perpendicular to the X-rays applied from the X-ray generator 6. FIG. 3 shows an example of the film cassette 21 replaceably loaded with an X-ray film and a sensitizing paper sheet. A conventional film cassette having been used generally is used here without modification as the film cassette 21.

Since the above-mentioned operations, and the basic configuration and operations of the main body 1 of the apparatus wherein a film cassette is used have been known, further explanation is omitted. However, as described later, in the apparatus in accordance with the present embodiment, a variety of circuits required when a digital sensor cassette is used are provided in the control portion 11. Furthermore, the X-ray detector 7 is provided with a connector 14 for connection to the digital sensor cassette.

Figure 4:
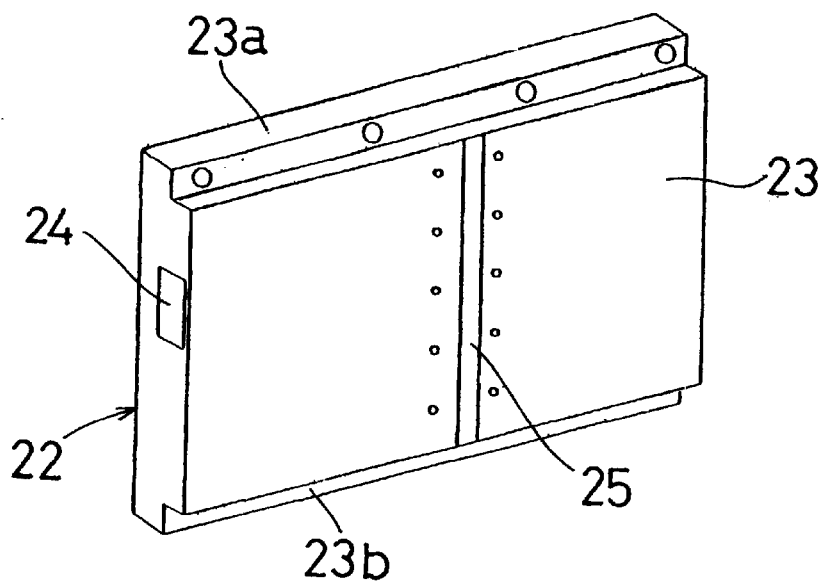
FIG. 4 is a perspective view showing an example of a digital sensor cassette used for the apparatus.

FIG. 4 shows an example of a digital sensor cassette 22 used for the apparatus. When a conventional film cassette having been used generally is used without modification as the film cassette 21 as described above, a cassette holder for the conventional film cassette can also be used without modification as the cassette holder 9. As shown in FIG. 2, the upper and lower edges of the cassette holder 22 are each, equipped with a cassette support piece 9c having a shape of L in cross section. Therefore, the dimensions and shape of the outer housing 23 of the digital sensor cassette 22 are made nearly identical with those of the film cassette 21. In particular, the dimensions and shapes of the upper edge 23a and the lower edge 23b of the outer housing 23 are selectively determined to have dimensions and shapes so as to be insertable and mountable in the space between the cassette support pieces 9c, 9c of the cassette holder 9.

The cassette holder 9 of the X-ray detector 7 should only be configured so that the film cassette 21 and the digital sensor cassette 22 can be mounted smoothly therein, one at a time. For example, without using the conventional film cassette having been used generally as the film cassette 21, by using the cassettes 21 and 22 specially made for this apparatus, the cassette holder 9 configured to be adapted for the special cassettes can also be adopted.

The digital sensor cassette 22 is equipped with an electric X-ray image detector and various circuits related thereto inside the outer housing 23. A connector 24 for connection to an external circuit is provided on one side of the housing 23. This connector 24 is usually connected to the connector 14 of the X-ray detector 7 by a cable integrally containing power lines and signal lines. In addition, the connector 24 can also be connected to an external device such as a personal computer. The outer housing 23 is formed of an appropriate material having necessary strength, for example metal, such as an aluminum sheet, or synthetic resin, such as ABS resin. At the front center of the outer housing 23, an X-ray receiver 25 formed of a material having high transmittance for X-rays and capable of shielding visible light, such as dark-colored ABS resin or the like, is provided in the vertical direction in correspondence with the secondary slit 8a. Inside the X-ray receiver 25, the electric X-ray image detector is disposed.

Figure 5:
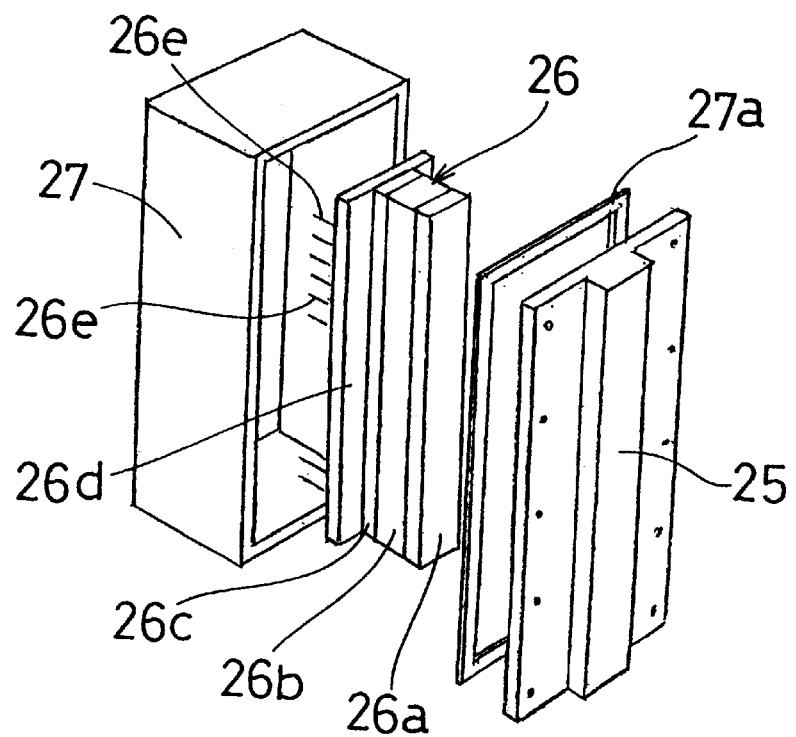
FIG. 5 is a perspective view showing the structure of the electric X-ray image detector of the digital sensor cassette.

FIG. 5 is a view showing the general structure of the electric X-ray image detector and a protection case for the detector. The electric X-ray image detector 26 has a three-layer structure comprising a light emitter for emitting light when irradiated with X-rays, i. e., a scintillator 26a, an optical fiber device 26b for transmitting the light emitted from the light emitter 26a, and an image pickup device portion 26c formed of a semiconductor sensor, such as CCD or MOS, having two-dimensionally disposed pixels of an image pickup device. This three-layer structure is integrally provided on a ceramic base 26d. The numeral 27 designates the protection case, and the numeral 27a designates a shield material.

In FIG. 5, the thicknesses of the components of the electric X-ray image detector 26 are exaggerated. The actual thicknesses of the components are as follows: the light emitter 26a is 0.3 mm, the optical fiber device 26b is; 1.5 mm, the image pickup device portion 26c is 0.5 mm, and the ceramic base 26d is 1 mm in thickness, for example. Furthermore, the pixel configuration of the image pickup device portion 26c is a two-dimensional arrangement of square pixels measuring 96 μm on each side and disposed so as to form a rectangle measuring about 6 mm in width and about 150 mm in length. The signals of the image pickup device portion 26c are taken out of electrodes 26e disposed on the back side of the ceramic base 26d.

The protection case 27 is formed of a lightproof material to eliminate the influence of visible light on the electric X-ray image detector 26. The electric X-ray image detector 26 is covered with this protection cover 27, and is also covered with the X-ray receiver 25 on the front side thereof. In this covered condition, the electric X-ray image detector 26 is housed In the housing 23. In the case that the housing 23 is lightproof, it is possible to omit the protection case 27.

Because of the above-mentioned configuration, a panoramic X-ray image can be obtained in the form of digital signals by the electric X-ray image detector 26. Since the image pickup device portion 26c comprises a semiconductor sensor, such as CCD or MOS, the digital sensor cassette 22 can have high sensitivity. In addition, while protected against visible light, the electric X-ray image detector 26 can smoothly receive X-rays, thereby making it possible to carry out clear radiographing.

Figure 10:
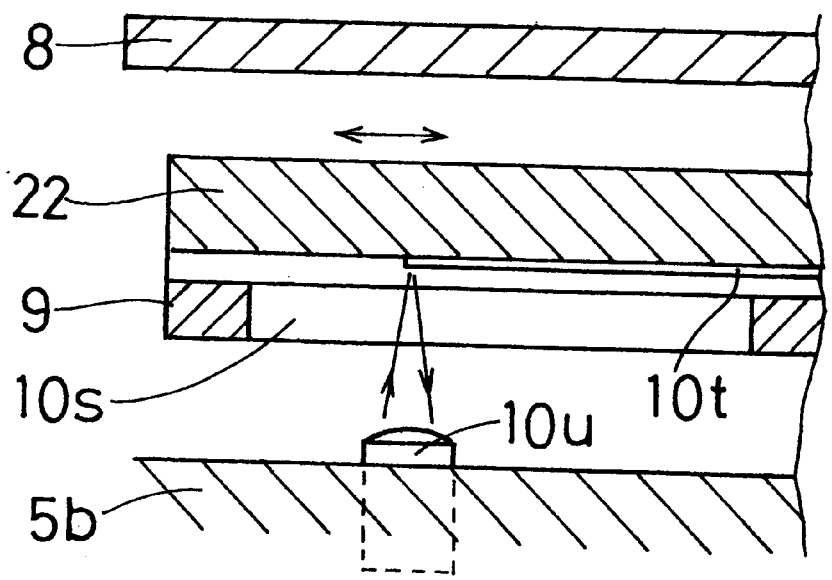
FIG. 10 is a partially cutaway plan view showing still another securing means for the digital sensor cassette.
Figure 11:
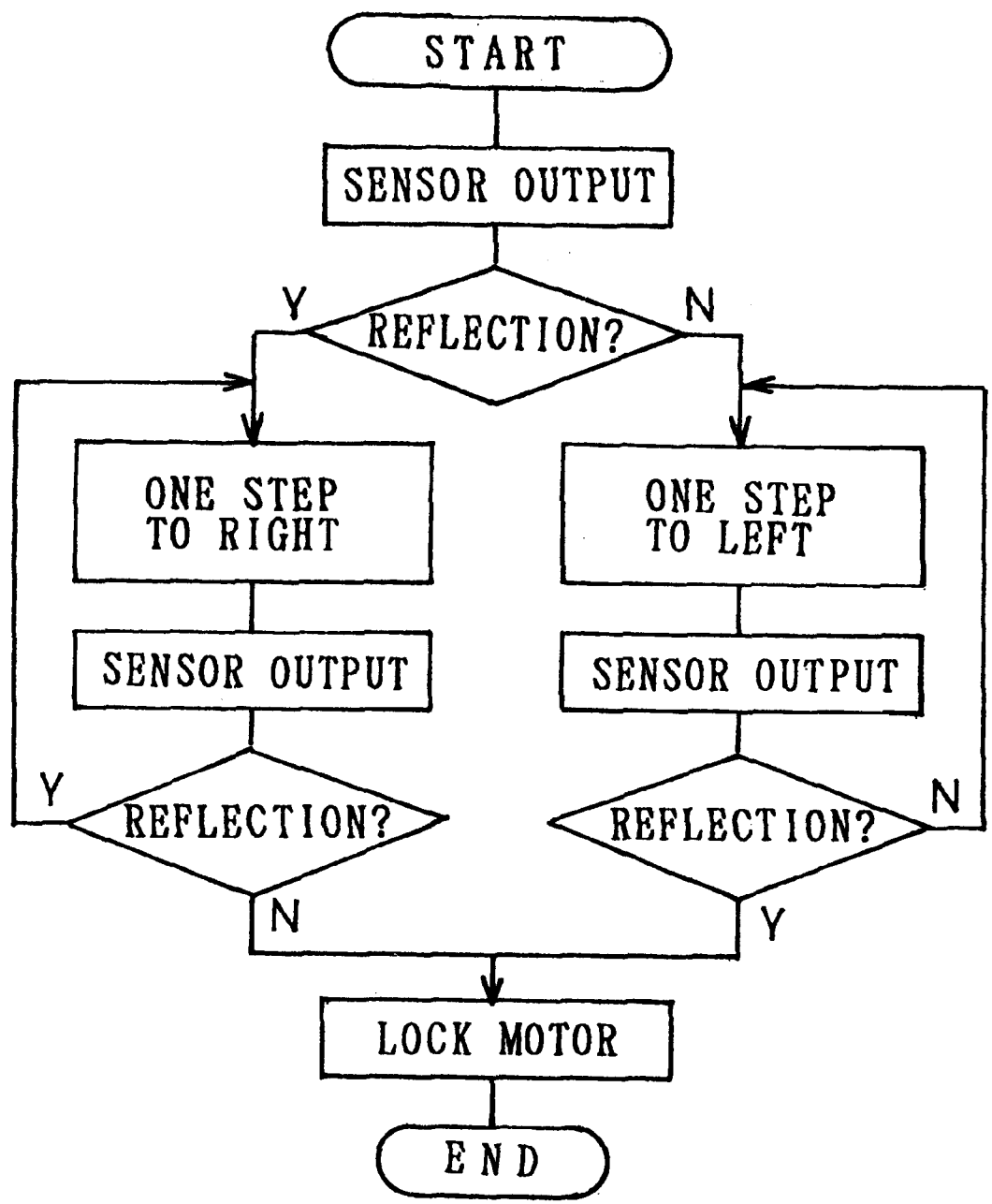
FIG. 11 is a flowchart showing a procedure of position control by the securing means shown in FIG. 10.

Next, means for positioning and securing the digital sensor cassette will be described below. FIGS. 6A to 9 show examples of mechanical means, and FIGS. 10 and 11 show examples of electrical means.

The cassette holder 9 is supported on the side of the end 5b of the rotary arm 5. Referring to FIGS. 6A and 6B, the numeral 9a-1 designates a sliding member on the arm side, secured to the end 5b, and the numeral 9a-2 designates a sliding member on the cassette holder side, secured to the back side of the cassette holder 9. A rod-like tightening member 10a having a male thread 10b at its end is secured with a clamp 10c to the sliding member 9a-1 on the arm side in the longitudinal direction thereof. In addition, as shown in FIGS. 7A and 7B, a mounting plate 10d is secured to one side of the digital sensor cassette 22 by screws, a positioning plate 10e is secured to the mounting plate 10d, and a tightening member 10f having a female thread log at its end is rotatably mounted on the mounting plate 10d.

Figure 8A:
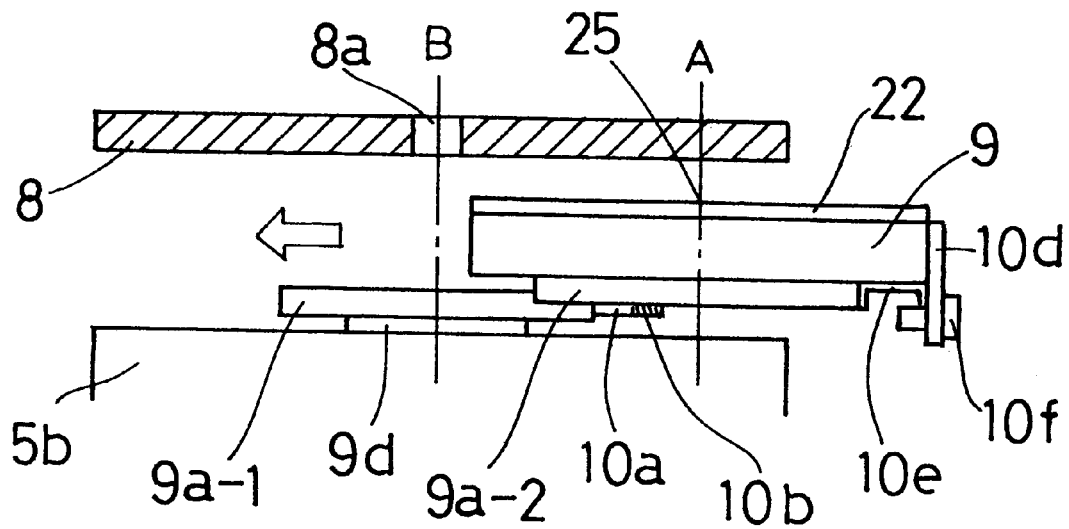
FIG. 8A is a plan view illustrating a method of mounting the digital sensor cassette.
Figure 8B:
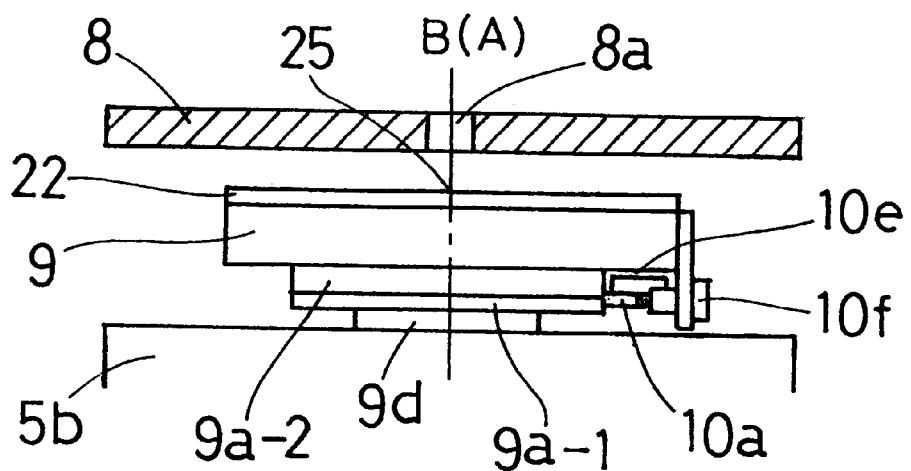
FIG. 8B is a plan view illustrating the method of mounting the digital sensor cassette.

A method of mounting the digital sensor cassette 22 in the X-ray detector 7 is described below. First, the cassette 22 is mounted in the cassette holder 9 as shown in FIGS. 6B and 8A. The end of the positioning plate 10e is made contact with the end surface of the sliding member 9a-2 on the cassette holder side. Since the length of the cassette holder 9 is the same as that of the digital sensor cassette 22, the center of the cassette holder 9 indicated by line A is aligned with the center of the digital sensor cassette 22 provided with the X-ray receiver 25 in this condition. Next, the cassette holder 9 and the digital sensor cassette 22 are moved and inserted in the direction indicated by the arrow on the back side of the shield plate 8 so that the positioning plate 10e makes contact with the end surface of the sliding member 9a-1 as shown in FIG. 8B. The dimensions of the members have been selectively determined so that the X-ray receiver 25 at the center of the digital sensor cassette 22 is aligned with the center of the secondary slit 8a of the shield plate 8 indicated by line B, and so that the female thread 10g of the tightening member 10f is positioned so as to be engaged with the male thread 10b of the tightening member 10a in this contact condition. By engaging the male thread 10b with the female thread log and by tightening the tightening member 10f, the digital sensor cassette 22 can be secured to a predetermined position.

Figure 9:
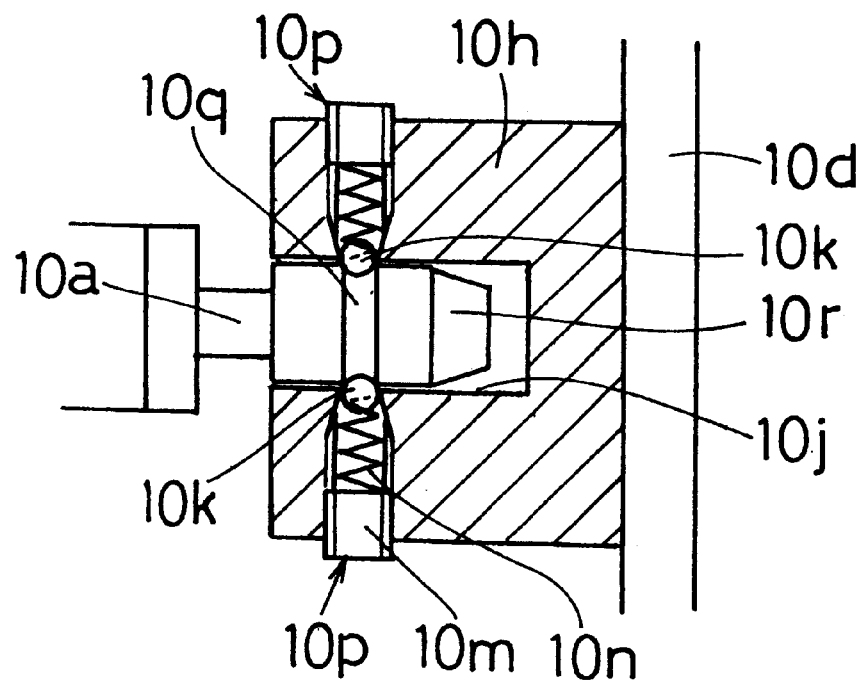
FIG. 9 is a partially cutaway plan view showing another securing means for the digital sensor cassette.

Instead of the above-mentioned thread engagement between the tightening member 10f and the tightening member 10a, a ball-plunger arrangement shown in FIG. 9 can also be used. In other words, instead of the tightening member 10f, a tightening member 10h having an engagement recess 10j is secured to the mounting plate 10d. Furthermore, the tightening member 10h is provided with an engagement portion 10p wherein balls 10k projecting into the engagement recess 10j are pushed by screws 10m and springs 10n. The end of the tightening member 10a is provided with an engagement member 10r having an engagement groove 10q corresponding to the engagement portion 10p. Because of this configuration, when the digital sensor cassette 22 is inserted to the predetermined position on the back side of the shield plate 8, the engagement member 10r is inserted into the engagement recess 10j, and the balls 10k of the engagement portion 10p engage the engagement groove 10q, whereby the digital sensor cassette 22 is positioned and secured at the same time. This securing can be released by pulling out the tightening member 10h by applying a force greater than the engagement force exerted between the engagement groove 10q and the balls 10k in correspondence with the pushing pressure of the springs 10n.

In an example using an electrical means shown in FIG. 10, a small slot 10s is provided at the end of the cassette holder 9. A reflection member 10t is provided at a position corresponding to the slot 10s on the back side of the digital sensor cassette 22, that is, at a position facing the slot 10s when the digital sensor cassette 22 is mounted in the cassette holder 9 so that the center of the digital sensor cassette 22 is aligned with the center of the cassette holder 9. The reflection member 10t is formed of a reflective sheet attached to the digital sensor cassette 22, for example. Furthermore, the end 5b of the rotary arm 5 is provided with a detection sensor 10u equipped with a light-emitting device and a photodetector device. The position of the detection sensor 10u is determined so as to face the reflection member 10t when the cassette holder 9 and the digital sensor cassette 22 are mounted at the predetermined position.

The cassette holder drive motor 9b is a stepping motor. After the digital sensor cassette 22 is mounted in the cassette holder 9 and moved nearly close to the predetermined position by hand, position control is carried out in accordance with such a procedure as that shown in FIG. 11, for example. More specifically, the output of the detection sensor 10u is read, and the drive motor 9b is moved one step to the right or left in accordance with the presence or absence of reflection, and the output of the detection sensor 10u is read again. This operation is repeated, and the motor is stopped and locked at a position wherein the result of the detection of the presence or absence of reflection is reversed. In other words, in accordance with this procedure, when the boundary of the side edge of the reflection member 10t has just reached the position facing the detection sensor 10u, a judgment is made that the digital sensor cassette 22 has been mounted at the predetermined position. Therefore, the positions of the reflection member 10t and the detection sensor 10u are determined to satisfy this condition.

Figure 12:
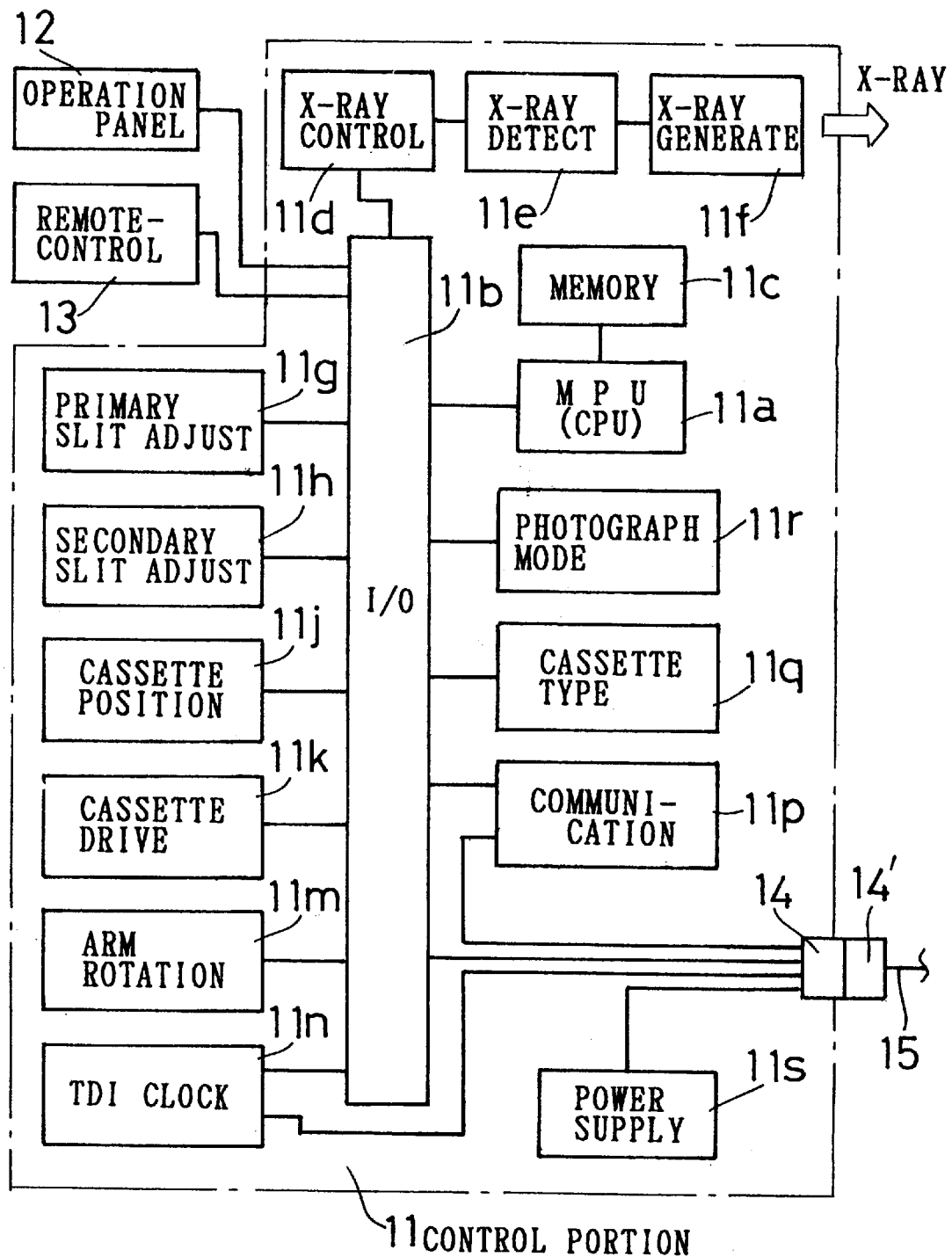
FIG. 12 is a block diagram of the control circuit of the apparatus.

As shown in FIG. 12, the control portion 11 comprises a control unit 11a, such as MPU or CPU, used as a central operation control unit for the entire apparatus, input/output ports 11b and a memory 11c. In addition, an X-ray irradiation control circuit 11d, an X-ray irradiation detection circuit 11e, an X-ray generation circuit 11f, a primary slit width adjustment circuit 11g, a secondary slit width adjustment circuit 11h, a cassette position detection circuit 11j, a cassette drive circuit 11k, a rotary arm rotation detection circuit 11m, a TDI clock generation circuit 11n and the like are provided, and these circuits are connected to the control unit 11a via the input/output ports 11b.

The above-mentioned circuits have also been provided basically in a conventional apparatus used with film cassettes. The apparatus in accordance with the present invention, however, further comprises a communication control circuit 11p, a cassette type detection circuit 11q, a photographing mode setting circuit 11r, a power supply circuit 11s and the like. These circuits, the various switches and the display portion on the operation panel 12, the various switches on the remote-control box 13 and the connector 14 are connected as shown in FIG. 12.

Figure 13:
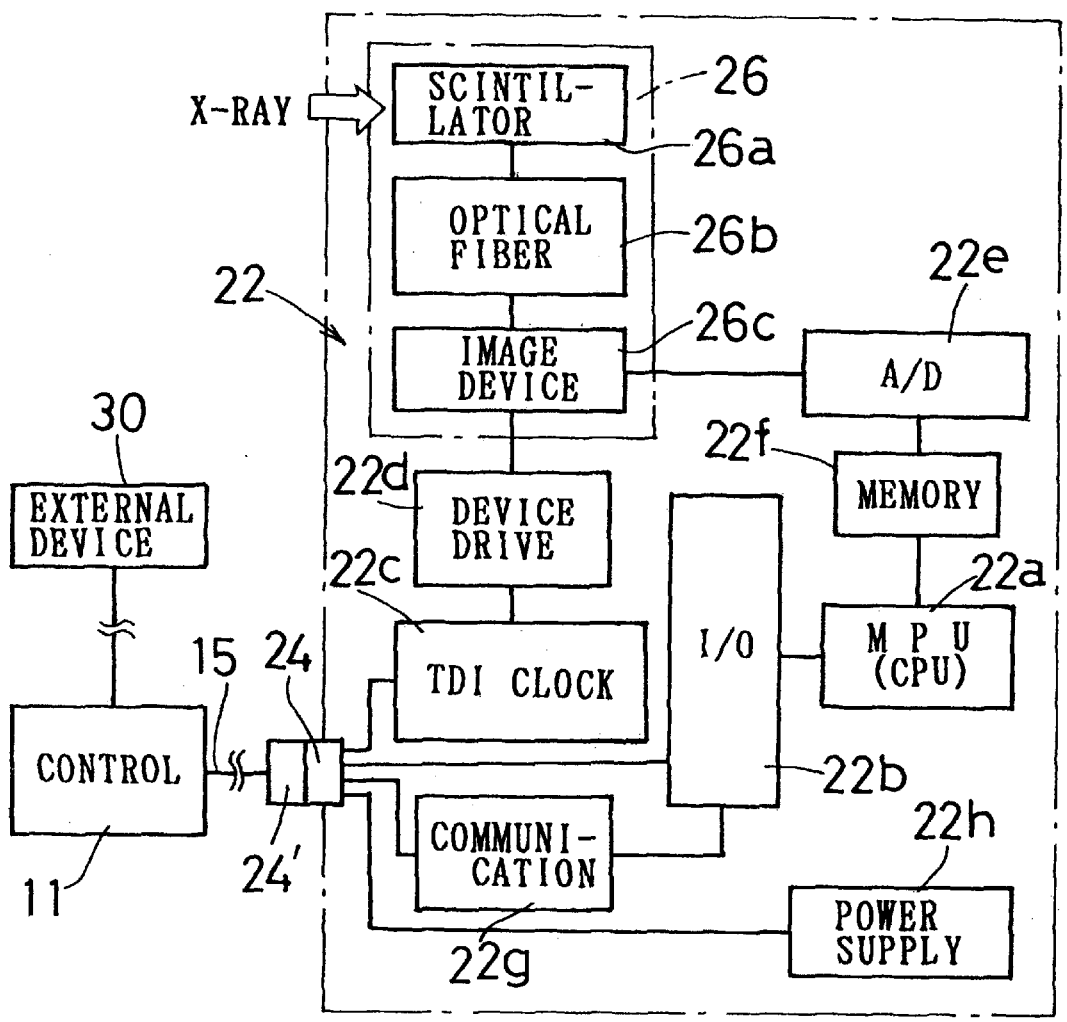
FIG. 13 is a block diagram of a control circuit of the digital sensor cassette.

Furthermore, as shown in FIG. 13, the digital sensor cassette 22 is provided with a control unit 22a, such as MPU or CPU, for controlling the operations of all the circuits in the cassette 22 and the operations of the entire apparatus including the main body 1 of the apparatus, independently or integrated with the control portion 11 of the main body 1 of the apparatus. The digital sensor cassette 22 is further provided with input/output ports 22b, a TDI clock conversion circuit 22c, an image pickup device drive circuit 22d, an A/D converter 22e, a memory 22f, a communication control circuit 22g, a power supply circuit 22h and the like. These circuits, the electric X-ray image detector 26 and the connector 24 are connected as shown in FIG. 13.

Next, panoramic radiographing by using the digital sensor cassette 22 will be described below referring to FIGS. 12 and 13. First, the digital sensor cassette 22 is mounted in the cassette holder 9. The cassette 22 is secured to the predetermined position by the above-mentioned means by operating the cassette position detection circuit 11j and the cassette drive circuit 11k. The connector 14 is connected to the connector 24 by using a cable 15 comprising wires or optical fibers and having a connector 14' on one end of the cable and a connector 24' on the other end, the connectors 14' and 24' being adapted to be connectable to the connectors 14 and 24, respectively. By the connections, a predetermined signal circuit is formed, and communication is made possible between the digital sensor cassette 22 and the main body 1 of the panoramic radiographic apparatus, whereby various signals are transmitted therebetween. When the mounting of the digital sensor cassette 22 is detected by the cassette type detection circuit 11q, the radiographing mode for the digital sensor cassette 22 is selected, and various conditions in accordance with this mode are set by the photographing mode setting circuit 11r, whereby preparations for photographing are carried out.

In this way, the type of a mounted cassette is detected by the cassette type detection circuit 11q, a photographing mode in accordance with the type of the cassette is automatically selected, and predetermined photographing conditions are set. This eliminates the need for the operator to select a photographing mode and to set photographing conditions in accordance with the type of the cassette to be used, thereby making the operation of the apparatus easy.

By making an arrangement so that the photographing mode for a film cassette is selected when the mounting of a digital sensor cassette is not detected, the automatic selection of the photographing mode is made possible even when a film cassette having no communication function is used.

Photographing is started by turning on the X-ray irradiation switch on the remote-control box 13. X-rays are applied from the X-ray generator 6 to the X-ray detector 7. At the same time, the rotation center of the rotary arm 5 is moved and the rotary arm 5 is rotated. At this time, the drive motor 9b of the cassette holder 9 is stationary, and a TDI clock signal delivered at the time of photographing by using an ordinary film cassette and synchronized with the rotation of the rotary arm 5, that is, a signal for time delay integration control, is transmitted to the digital sensor cassette 22 by the rotary arm rotation detection circuit 11m and the control unit 11a. In accordance with this transmission of the signal, the image pickup device portion 26c is driven. The TDI clock signal is supplied in a digital or analog form, and the cassette 22 is configured to receive both types of signals.

When the image pickup device portion 26c is driven, linear X-ray image information required for generating a panoramic X-ray image is delivered sequentially from the electric X-ray image detector 26, and transferred to the memory 22f via the A/D converter 22e. Generating a panoramic X-ray image is carried out sequentially beginning with its end, and the image is stored. These operations are carried out during a period between the transmission/reception of an X-ray irradiation start signal and the transmission/reception of an X-ray irradiation stop signal. The image process conducted at this time is an electrical process replaced with the process in accordance with the principle of obtaining panoramic X-ray images by using a method wherein a linear X-ray image is subjected to photosensing sequentially while a film cassette is moved in synchronization with the rotation of the rotary arm.

As clearly disclosed by the above descriptions, both the film cassette and the digital sensor cassette can be used with the apparatus shown in the figures, one at a time, whereby desired panoramic X-ray images can be obtained by fully using the features of each type of cassette. In particular, the digital sensor cassette does not require development, whereby a panoramic X-ray image can be obtained immediately, thereby being applicable to diagnosis using computers. Furthermore, by slightly modifying an existing widespread panoramic radiographic apparatus used with a film, it is possible to obtain an apparatus which can be used with the digital sensor cassette in accordance with the present invention as well as the film.

The amount of X-ray dose in the case of the photographing mode for the digital sensor cassette can be less than that in the case of the photographing mode for the film cassette, because the sensitivity of the electric X-ray image detector 26 is higher than that of the film. Owing to this reduction in the amount of X-ray dose, the amount of X-ray exposure to the subject to be photographed can be reduced. In this case of using the digital sensor cassette 22, when the mounting of the digital sensor cassette 22 is detected, the X-ray irradiation control circuit 11$d$ is automatically controlled on the side of the main body of the panoramic radiographic apparatus depending on the type of the semiconductor sensor, such as CCD or MOS for example, used for the image pickup device 26$c$. and the voltage and current of the X-ray tube are set to appropriate values. However, it is possible to set the values by designating appropriate values on the side of the digital sensor cassette 22.

The communication between the digital sensor cassette 22 and the main body 1 of the panoramic radiographic apparatus is carried out under the control of the communication control circuit 11$p$. In mutual communication other than described above, information about the cassette, such as the serial number, photographing preparation conditions and operation conditions of the cassette, are transmitted from the cassette, and some operations of the main body 1 of the apparatus are controlled in accordance with the information about the operation conditions. Even when operations which cannot be conducted simultaneously are attempted by using commands during data processing or transfer on the side of the main body 1 of the apparatus, such commands are not accepted. As a result, malfunctions are prevented, and the reliability of operation is raised.

Furthermore, in addition to the above-mentioned TDI clock signal, various pieces of information about photographing, such as a photographing mode, photographing preparation conditions, X-ray irradiation start/stop, X-ray tube voltage and current and an area to be photographed are included in the information transmitted from the control portion 11. These pieces of information can be used to obtain appropriate panoramic X-ray images, or used for diagnosis after photographing. The primary and secondary slits are adjusted in the case of narrow slit photographing, and the conditions of the adjustments are transmitted. In the case of 4-split photographing, information about the area to be photographed and the like is also transmitted.

X-ray image information delivered from the electric X-ray image detector 26 may be stored in the memory 11$c$ of the control portion 11 of the main body of the apparatus, instead of the memory 22$f$ of the digital sensor cassette 22. Furthermore, as shown in FIG. 13, via the control portion 11 of the main body 1 of the panoramic radiographic apparatus connected to the connector 24, the apparatus can be connected to an external device 30, such as a personal computer or a large computer, or a network of these devices, and in this connection condition, a panoramic X-ray image can be indicated in real time on the display of the external device. It is also possible to connect the external device 30 to the connector 24 after photographing to directly transfer an image to the external device 30.

By using a device having a high processing capability as the external device 30, it is possible to display not only panoramic X-ray images, but also data concerning photographing, such as a photographing mode, tube voltage, tube current and an area to be photographed. Moreover, it is possible to register these together with data concerning each patient, such as a patient name and ID number so as to use them for diagnosis after photographing. In this way, a variety of uses are made possible.

Figure 14:
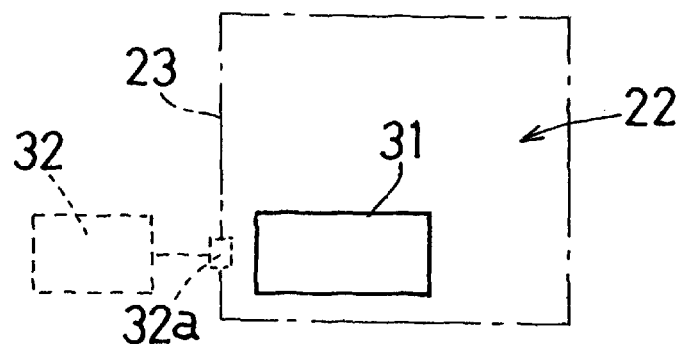
FIG. 14 is a block diagram of another control circuit of the digital sensor cassette.

Electric power can be supplied to the digital sensor cassette 22 via the connector 24, or via a power connection portion provided separately. However, since the digital sensor cassette 22 is an active device equipped with the memory 22$f$ and the control unit 22$a$, the application range of the cassette 22 can be expanded by using a dry cell or a secondary battery built inside or connected externally as a power supply. FIG. 14 is a view showing an example wherein a secondary battery 31 is mounted additionally in the configuration shown in FIG. 13. Instead of mounting the secondary battery 31 in the housing 23, an external battery 32 may be connected to a battery connection portion 32$a$ disposed at an appropriate position in the housing 23 via required lead wires, or directly connected to the battery connection portion 32$a$ by using a removable connector capable of mechanical clamping. With such a configuration, it is not necessary to provide a power supply circuit on the main body side of the panoramic radiographic apparatus, and no power cable is required. Therefore, the panoramic radiographic apparatus used with film cassettes can easily be modified to an apparatus capable of using digital sensor cassettes.

Furthermore, when the secondary battery 31 is mounted as described above in particular, no power cable is required to be connected. Besides, instead of using wire communication requiring cables, by using wireless communication, no cable is required for communication. Since both cables for power and communication are not required, connection work can be saved, thereby enhancing rationalization. In this case, a non-contact wireless communication means, such as a means using infrared rays or radio waves, should only be added to the configurations shown in FIGS. 12 and 13, and the connector 24 can be omitted. Even when the secondary battery 31 is not mounted in the digital sensor cassette 22, it is needless to say that a wireless type can be used as a communication means.

Figure 15:
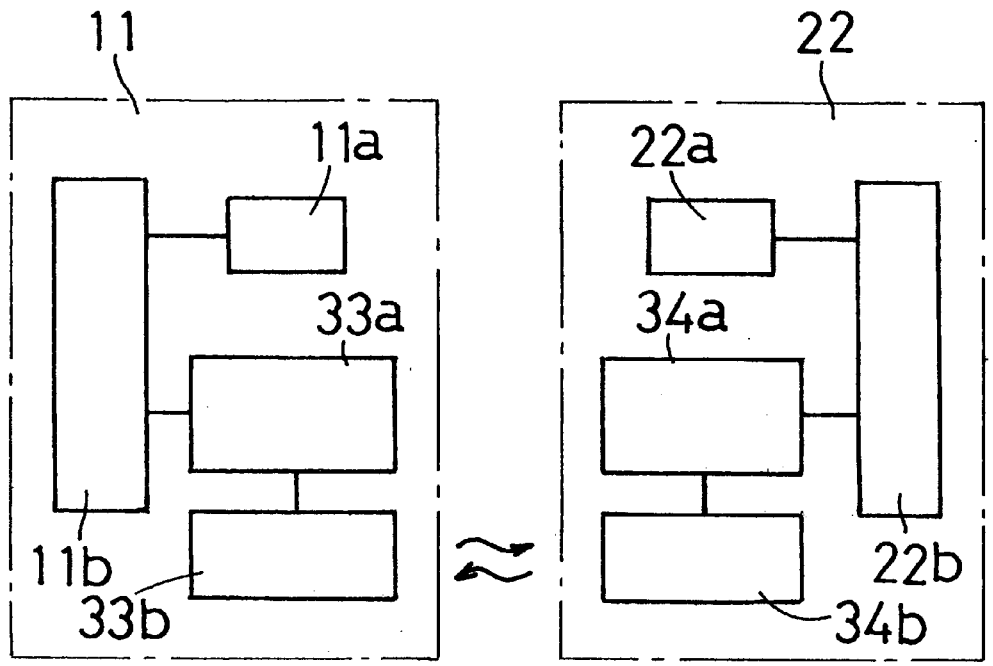
FIG. 15 is a block diagram of still another control circuit of the digital sensor cassette.

FIG. 15 shows an example of an infrared communication means. The control portion 11 of the main body of the panoramic radiographic apparatus is provided with an infrared control circuit 33$a$ and its transmission/reception portion 33$b$. The digital sensor cassette 22 is provided with an infrared control circuit 34a and its transmission/reception portion 34b. As the transmission/reception portions 33b and 34b, a light-emitting diode and a photo transistor are used. The light-emitting diode and the photo transistor are disposed so as to face each other when the digital sensor cassette 22 is mounted in the cassette holder 9. In particular, when the light-emitting diode and the photo transistor are disposed to face very close to each other, the output can be made smaller, and the performance can be less affected by interference.

Figure 16:
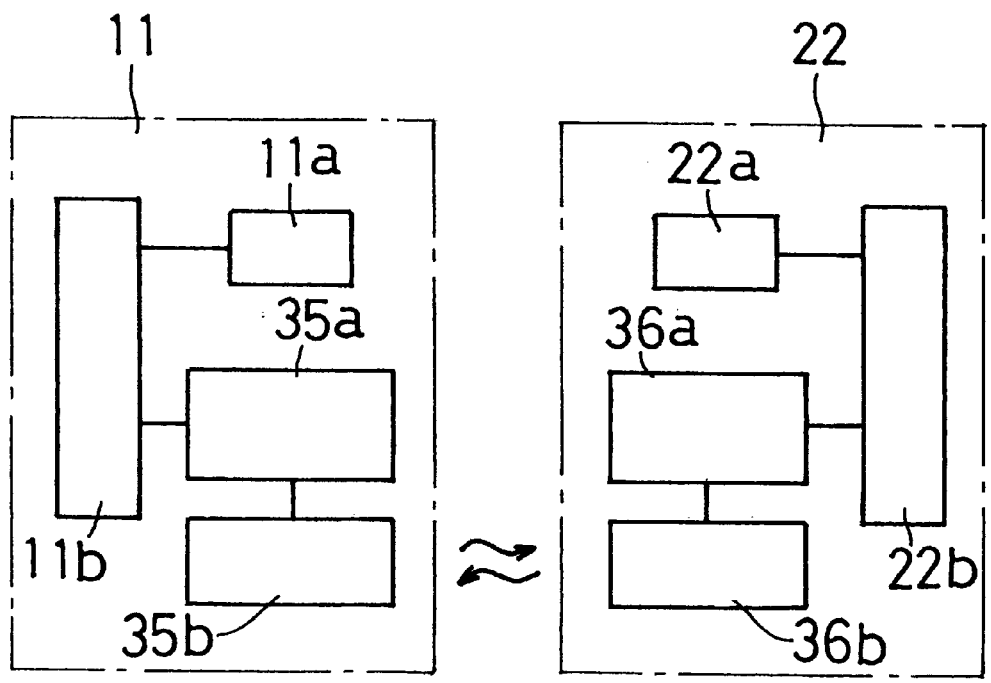
FIG. 16 is a block diagram of yet still another control circuit of the digital sensor cassette.

FIG. 16 shows an example of a radio wave communication means. The control portion 11 of the main body of the apparatus is provided with a radio wave control circuit 35a and its transmission/reception portion 35b. The digital sensor cassette 22 is provided with a radio wave control circuit 36a and its transmission/reception portion 36b. The frequency of a radio wave and the type of modulation may be those adopted appropriately. Therefore, the locations of the transmission/reception portions 35b and 36b can be selectively determined more freely than those in the case of the infrared type.

Figure 17:
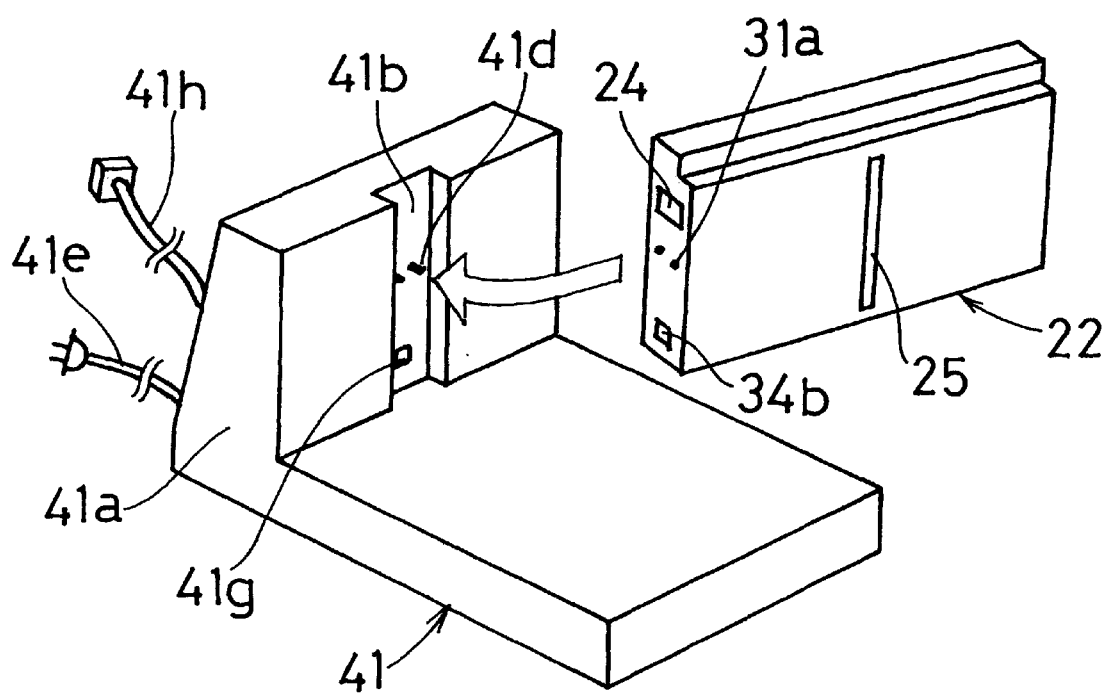
FIG. 17 is a view showing a method of mounting the digital sensor cassette in a charger for the digital sensor cassette.
Figure 18:
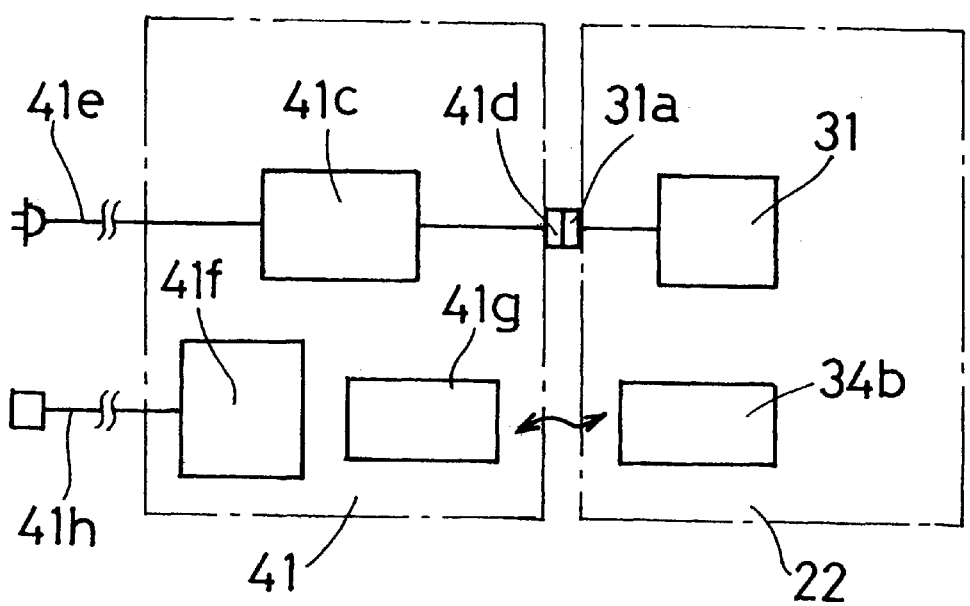
FIG. 18 is a block diagram showing control circuits of the charger and the digital sensor cassette.

When the secondary battery 31 is mounted in the digital sensor cassette 22 as a power supply as shown in FIG. 14, the battery must be replaced or charged. FIGS. 17 and 18 show an example of a charger 41 used to charge the secondary battery 31 while the battery is kept mounted in the digital sensor cassette 22. A mounting portion 41b for accommodating the digital sensor cassette 22 is formed in a housing 41a, and the output portion 41d of a built-in charging circuit 41c is provided in the mounting portion 41b. In correspondence with this mounting portion 41b, the charge input portion 31a of the secondary battery 31 is provided on one end of the cassette 22. By inserting the end in the mounting portion 41b as indicated by the arrow shown in FIG. 17, the output portion 41d can be connected to the charge input portion 31a so as to charge the secondary battery 31. The numeral 41e designates a power cord connected to commercial electric power.

Furthermore, the charger 41 is provided with a communication circuit in correspondence with the communication type of the digital sensor cassette 22. For example, in the case that the cassette 22 is provided with the infrared transmission/reception portion 34b shown in FIG. 18, the charger 41 is provided with an infrared control circuit 41f and its transmission/reception portion 41g in correspondence with the transmission/reception portion 34b. The transmission/reception portion 41g is disposed at the mounting portion 41b, for example. In correspondence with the transmission/reception portion 41g, the transmission/reception portion 34b of the cassette 22 is disposed at a position facing the transmission/reception portion 41g when the cassette 22 is mounted in the mounting portion 41b. The numeral 41h designates a connection cord for connection to the external device. In the case that the cassette 22 is provided with a radio wave communication means or a wire communication means, the communication means of the charger 41 should only be a type compatible with the communication means. Alternatively, the charger 41 may be provided with all types of communication means so that it can be compatible with a variety of cassettes.

With these configurations, communication can be carried out between the charger 41 and the digital sensor cassette 22 while the secondary battery 31 is charged. It is thus possible to communicate with the external device via the charger 41 when the charger 41 is connected to the external device via the connection cord 41h. Therefore, by transferring a variety of data stored in the memory 22f to the external device, data processing, such as registration in database for use in image reproduction and diagnosis after photographing, can be carried out by effectively using the time for charging.

By using the second battery 31 as a power supply as described above, no power supply circuit is required for the main body of the panoramic radiographic apparatus. Therefore, the apparatus used with film cassettes can easily be modified so that the apparatus can be used with digital sensor cassettes. In addition, the trouble of preparing and connecting a power cable is unnecessary.

Furthermore, the secondary battery 31 can be charged by mounting the cassette 22 In the charger 41, and communication to the external device can be carried out via the charger 41 during charging. Therefore, data can be transferred to the external device by effectively using the time for charging. For these reasons, data processing for reproduction of images, diagnosis after photographing and the like can be rationalized.

What is claimed is:

1. A panoramic radiographic apparatus having a support for rotatably supporting a rotary arm provided with an X-ray generator at one end thereof and an X-ray detector at the other end thereof, comprising a cassette holder capable of accommodating both a film cassette loaded with an X-ray film and a digital sensor cassette loaded with an electric X-ray image detector, one at a time, at said X-ray detector, and a control means for performing electric control so that when a film cassette is mounted in said cassette holder, said cassette holder accommodating said film cassette is mechanically moved in accordance with the rotation of said rotary arm at a predetermined speed in a direction nearly perpendicular to X-ray beams applied from said X-ray generator to said X-ray detector so as to carry out panoramic radiographing using a film, and so that when a digital sensor cassette is mounted in said cassette holder, with said cassette holder accommodating said digital sensor cassette being in a secured condition with respect to said X-ray detector, said electric X-ray image detector is driven by supplying control signals corresponding to the rotation of said rotary arm from a main body of said panoramic radiographic apparatus to said digital sensor cassette to obtain image signals required for generating a panoramic X-ray image.

2. A panoramic radiographic apparatus in accordance with claim 1, comprising a detection means for detecting a film cassette or a digital sensor cassette mounted in a cassette holder, wherein the photographing mode for said film cassette or the photographing mode for said digital sensor cassette depending on the type of cassette is automatically selected, and photographing conditions in accordance with the selected mode are set.

3. A panoramic radiographic apparatus in accordance with claim 1 or 2, wherein said digital sensor cassette comprises said electric X-ray image detector for converting X-rays into electric signals, and further comprises at least an input/output portion for communication to an external circuit and a control portion for electrically controlling the operations of said X-ray image detector and said input/output portion.

4. A panoramic radiographic apparatus in accordance with claim 3, wherein control signals supplied from said main body of said panoramic radiographic apparatus to said digital sensor cassette by communication through said input/output portion include, in addition to a clock signal for time delay integration control in correspondence with the rotation of said rotary arm, information about photographing, at least X-ray irradiation start/stop, X-ray tube voltage and current and an area to be photographed.

5. A panoramic radiographic apparatus in accordance with claim 4, wherein operation signals indicating the operation conditions of said digital sensor cassette are delivered from said digital sensor cassette to said main body of said panoramic radiographic apparatus by communication through said input/output portion, and the operations of said main body of said panoramic radiographic apparatus are controlled by said operation signals.

6. A panoramic radiographic apparatus in accordance with claim 3, wherein by communication through said input/output portion, said detection means is used to detect whether said digital sensor cassette has been mounted or not, when the mounting of said digital sensor cassette is detected, the photographing mode for said digital sensor cassette is selected, and when the mounting of said digital sensor cassette is not detected, the photographing mode for said film cassette is selected.

7. A panoramic radiographic apparatus in accordance with claim 6, wherein conditions in the photographing mode for said digital sensor cassette include a condition wherein the amount of X-ray dose from said X-ray generator in the photographing mode for said digital sensor cassette is less than that in the photographing mode for said film cassette.

8. A panoramic radiographic apparatus in accordance with claim 7, wherein conditions in the photographing mode for said digital sensor cassette include a condition wherein said digital sensor cassette is secured in said X-ray detector without driving said cassette holder.

9. A panoramic radiographic apparatus in accordance with claim 8, wherein said digital sensor cassette is secured to a predetermined position in said X-ray detector by establishing mutual mechanical connection between a tightening member provided in said X-ray detector on said main body side and a tightening member provided on said digital sensor cassette.

10. A panoramic radiographic apparatus in accordance with claim 8, wherein a detector comprising a light-emitting device and a photodetector device provided in said X-ray detector detects the position of a reflection portion provided on said digital sensor cassette, said digital sensor cassette is moved to the predetermined position in said X-ray detector by driving a cassette holder drive motor provided in said X-ray detector, and then said digital sensor cassette is secured by keeping said motor stationary.

* * * * *

UNITED STATES PATENT AND TRADEMARK OFFICE
CERTIFICATE OF CORRECTION

PATENT NO.    : 6,219,401 B1
DATED         : April 17, 2001
INVENTOR(S)   : Akifumi Tachibana et al.

It is certified that error appears in the above-identified patent and that said Letters Patent is hereby corrected as shown below:

<u>Title page,</u>
Item [54], Title, change "Panoramic Radiographic Apparatus and Digital Sensor Cassette used for same Apparatus" to -- PANORAMIC RADIOGRAPHIC APPARATUS --

Signed and Sealed this

Eighteenth Day of June, 2002

*Attest:*

*Attesting Officer*

JAMES E. ROGAN
*Director of the United States Patent and Trademark Office*